United States Patent
Walser

(10) Patent No.: US 6,713,501 B1
(45) Date of Patent: Mar. 30, 2004

(54) SUPPLEMENT FOR DIALYSIS PATIENTS

(75) Inventor: Mackenzie Walser, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/582,819

(22) PCT Filed: Mar. 13, 1998

(86) PCT No.: PCT/US98/03815

§ 371 (c)(1), (2), (4) Date: Aug. 21, 2000

(87) PCT Pub. No.: WO99/34813

PCT Pub. Date: Jul. 15, 1999

(51) Int. Cl.[7] .................... A61K 31/415; A61K 31/195; A61K 31/40
(52) U.S. Cl. ................... 514/399; 514/561; 514/567; 514/419; 514/562
(58) Field of Search ............................... 514/399, 561, 514/567, 419, 562

(56) References Cited

U.S. PATENT DOCUMENTS 3,764,703 A  10/1973  Bergstrom et al. .......... 424/319

OTHER PUBLICATIONS

Furth et al, The Americal Journal of Clinical Nutrition, vol. 33, pp. 1387–1395, Jul. 1980.*
115CA:142315, Takagi et al, 1991.*
Furst et al, Effects of nutrition and catabolic stress on intracellular amino acid pools in uremia. The American Journal of Clinical Nutrition, vol. 33, Jul. 1980, pp. 1387–1395, see entire document.

* cited by examiner

Primary Examiner—Russell Travers
(74) Attorney, Agent, or Firm—Morgan, Lewis & Bockius LLP

(57) ABSTRACT

Use of a tablet diet supplement for administration to a dialysis patient comprising a mixture of L-histidine, L-isoleucine, L-leucine, L-lysine, L-methionine, L-phenylalanine, L-threonine, L-tryptophan, L-tyrosine and L-valine, for preventing and/or correcting hypoalbuminemia in a patient on dialysis.

2 Claims, No Drawings

SUPPLEMENT FOR DIALYSIS PATIENTS

BACKGROUND

The invention relates to an amino acid supplement for dialysis patients.

Patients on dialysis in the U.S. exhibit a 24% mortality per year. The best predictor of mortality identified to date is the serum albumin concentration. Small differences in serum albumin concentration predict substantial changes in mortality. For example, dialysis patients with a 0.2 g/dl higher serum albumin experience a mortality rate which is 25% lower (Owen et al., NEJM 329: 1001–6, 1993). Hypoalbuminemia is common at the onset of dialysis and during dialysis. It is not Amenable to dietary counseling in most cases. Its mechanism is unknown.

It has previously been shown that patients who have been prescribed a very low protein diet supplemented by either essential amino acids or ketoanalogues thereof for at least six months prior to dialysis rarely exhibit hypoalbuminemia at the onset of dialysis (Walser, M., Kidney Internat 44: 1139, 1993), in contrast to the national experience. It has also been shown that such patients have a substantially lower mortality on dialysis, in comparison with the national experience, at least for the first two years, despite consuming the usual dialysis diet (Coresh, J., M. Walser, and S. Hill; J Amer Soc Nephrol 6: 1379, 1995). Whether or not this reduction in mortality can be explained by higher levels of serum albumin could not be ascertained, because these patients were dialyzed at many facilities in several states.

The foregoing observations raise the possibility that supplementation of the diet of the dialysis patients with essential amino acids may protect against hypoalbuminemia, even in patients consuming normal or nearly normal quantities of dietary protein. No mechanism for such an effect is apparent, but similarly, no mechanism for the prevalence of hypoalbuminemia in this population has been identified, although several abnormalities of plasma and intracellular amino acid concentrations have been observed.

There are at least seven small clinical trials of oral supplementation with essential amino acids in dialysis patients reported (1–7). However none of these studies is definitive or well controlled. In reviewing these studies, Kaysen (8) states "Oral nutritional supplementation does not reverse hypoalbuminemia in this patient population"; Wolfson (9) states "However, despite a number of studies (reviewed subsequently) of the use of amino acid supplements, the impact on overall nutritional status has remained controversial"; Ikizler and Hakim (10) state "Furthermore, most of these studies are not controlled and are small in scope and the degree of success is variable".

Intravenous supplementation has been studied more extensively, but the expense of this treatment is prohibitive, and according to Wolfson (9), " . . . there are numerous flaws in many of these studies".

Furst et al. (11) designed a new formula of essential amino acids, with a higher proportion of valine, lower proportions of leucine and isoleucine, and the inclusion of tyrosine, in an attempt to correct the extracellular and intracellular abnormalities of amino acid concentration that they found in predialysis uremic patients. They have shown that this mixture maintains nitrogen balance while improving abnormalities of amino acid concentrations (11–14). This formula was also used in the Feasibility Phase of a large NIH-supported study entitled "Modification of Diet in Renal Disease", and was found to maintain nutrition in these patients with advanced chronic renal failure (15). This mixture has neither been used nor advocated in patients on dialysis.

SUMMARY OF THE INVENTION

The invention is based on the concept that a mixture of amino acids in tablet form and comprising, in each tablet, L-histidine 45 mg, L-isoleucine 60 mg, L-leucine 90 mg, L-lysine 65 mg, L-methionine 90 mg, L-phenylalanine 70 mg, L-threonine 65 mg, L-tryptophan 25 mg, L-tyrosine 75 mg, and L-valine 135 mg, administered in a dose of 8 to 18 tablets per day, will prevent and/or correct hypoalbuminemia in patients on dialysis (either hemodialysis or peritoneal dialysis), and will therefore improve their survival.

To illustrate the invention, a group of hypoalbuminemic dialysis patients is randomized to receive either these tablets (14 per day) or a similar placebo for three months, in a double-blind fashion, with no change in their diet. Randomization is stratified for two ranges of serum albumin concentration (low and very low) and for hemodialysis vs. peritoneal dialysis. Before supplementation and at monthly intervals during supplementation, serum albumin, anthropometry, and serum amino acid levels are measured. Patients receiving the amino acid supplement should exhibit a greater rise in serum albumin concentration than patients receiving the placebo. Since serum albumin concentration is the best predictor of mortality, patients receiving the amino acid supplement are also anticipated to exhibit lower mortality.

It will be appreciated that the invention contemplates variations in the amounts of amino acids from those recited above. Typically the variation can be in the order of 10–30% by weight. However, it is preferred that the indicated ratios of the amino acids be maintained. Thus, for example, the amounts of L-leucine and L-methionine should be about twice the amount of L-histidine administered while the amount of L-isoleucine should be about two-thirds of the L-leucine and L-methionine.

Reference

1. Phillips M E, Havard J, Howard J P. Oral essential amino acid supplementation in patients on maintenance hemodialysis. Clin Nepbrol 9, 241–248, 1978.
2. Hecking E, Kohler H, Zobel R., Lemmel E-M, Mader H, Opferkuch W, Prellwitz W, Keim H J, Muller D. Treatment with essential amino acids in patients on chronic hemodialysis; a double blind cross-over study. Am J Clin Nutr 31, 1821–1826, 197.
3. Ulm A, Neuhauser M, Leber H-W. Influence of essential amino acids and keto acids on protein metabolism and anemia of patients on intermittent hemodialysis, Am J Clin Nutr 31, 1827–1830, 1978.
4. Counahan R, El-Bishti M, Chantler C. Oral essential amino acids in children on regular hemodialysis. Clin Nephrol 9: 11–14, 1978.
5. Acchiardo S, Moore L, Cockrell S. Effect of essential amino acids on chronic hemodialysis patients. ASAIO Trans 28, 608–614, 1982.
6. Knefati Y, Wone C, Aparicio M. Protein malnutrition of CAPD patients could be treated by oral mixtures of ketoacids and essential amino acids (KA/AA)(Abstract). Kidney Internat 36, Suppl 27, S-303, 1989.
7. Ecder S T, Tuna S, Sever M S, Ozdogan, Ark E, Aysuna N, Bozfakioglu S, Ergin Karadayi H, Aydin A E, Kocak N. Effects of orally administered essential amino acids on patients undergoing maintenance haemodialysis therapy (Abstract) Nephrol Dial Transplant 9; 100, 1994.

8. Kaysen G A. Hypoalbuminemia in dialysis patients. Seminars in Dialysis 9: 249–256, 1996.
9. Wolfson M. Use of nutritional supplements in dialysis patients. Seminars in Dialysis 5: 285–290, 1992.
10. Ikizler T A, Hakim R M. Nutrition in end-stage renal disease. Kidney Internat 50: 343–357, 1996.
11. Furst P, Alvestrand A, Bergstrom J. Effects of nutrition and catabolic stress on intracellular amino acid pools in uremia. Am J Clin Nutr 33: 1387–95, 1980.
12. Alvestrand A, Furst P. Bergstrom J. Plasma and muscle amino acids in uremia: influence of nutrition with amino acids. Clin Nephrol 18: 297–305, 1982.
13. Alvestrand A, Ahlberg M, Furst P, Bergstrom J. Clinical results with a low protein diet and a new amino acid preparation in patients with chronic uremia. Clin Nephrol 19: 67–73, 1983.
14. Bergstrom J, Ahlberg M, Alvestrand A, Furst P. Amino acid therapy for patients with chronic renal failure. Infusionsther Klin Ernahr 14: Suppl 5: 8–11, 1987.
15. Modification of Diet in Renal Disease Study Group. The Modification of Diet in Renal Disease Study: design, methods, and results from the Feasibility Study. Am J Kidney Dis 20: 18–33, 1992.

What is claimed is:

1. A method of correcting hypoalbuminemia in a patient on hemodialysis which comprises orally administering to the patient an effective amount of a composition comprising a mixture of L-histidine, L-isoleucine, L-leucine, L-lysine, L-methionine, L-phenylalanine, L-threonine, L-tryptophan, L-tyrosine and L-valine and continuing said administration to increase serum albumin concentration.

2. The method of claim 1 wherein the composition as administered comprises a mixture of the indicated components in a weight ratio as represented by the following: L-histidine 45 mg, L-isoleucine 60 mg, L-leucine 90 mg, L-lysine 65 mg, L-methionine 90 mg, L-phenylalanine 70 mg, L-theronine 65 mg, L-tryptophan 25 mg, L-tyrosine 75 mg, and L-valine 135 mg.

* * * * *